United States Patent [19]

Seng et al.

[11] Patent Number: 4,939,176

[45] Date of Patent: Jul. 3, 1990

[54] VIRAL INACTIVATION PROCESS

[75] Inventors: Richard L. Seng, Guerneville; John L. Lundblad, El Cerrito, both of Calif.

[73] Assignee: Miles Inc., Elkhart, Ind.

[21] Appl. No.: 287,368

[22] Filed: Dec. 20, 1988

[51] Int. Cl.$^5$ .................. A61K 31/045; A61K 35/14; A61K 39/104; A61K 39/395

[52] U.S. Cl. ...................... 514/724; 424/86; 424/87; 424/88; 424/89; 530/363; 530/380; 530/381; 530/382; 530/383; 530/387

[58] Field of Search ............... 530/363, 380, 381, 382, 530/383, 387; 424/86, 87, 88, 89; 514/724

[56] References Cited

U.S. PATENT DOCUMENTS

| | | | |
|---|---|---|---|
| 4,440,679 | 4/1984 | Fernandes et al. | 530/363 |
| 4,446,134 | 5/1984 | Naito et al. | 424/101 |
| 4,481,189 | 11/1984 | Prince | 424/101 |
| 4,495,278 | 1/1985 | Thomas | 435/5 |
| 4,534,972 | 8/1985 | Lembach | 424/86 |
| 4,762,714 | 8/1988 | Mitra et al. | 530/387 |
| 4,834,975 | 5/1989 | Siadak et al. | 424/87 |

OTHER PUBLICATIONS

"New Immunotype Schema for *Pseudomonas Aeruginosa* Based on Protective Antigens", Fisher et al., Journal of Bacteriology, pp. 835–836, vol. 98, No. 2, May 1969.

"Anti-Microbial Agents and Chemotherapy", J. A. Sands et al., pp. 134–136, Jan. 1979.

Sequential Use of Fatty Acids, Horowitz et al., Vox. Sang., 54:14–20 (1988).

Precipitation of Plasma Proteins, Steinbuch et al., Biochem. Biophys., 134, 279–294 (1969).

IgG Recovery Using Caprylic Acid, Russo et al., J. Immunol. Methods, 65, 269–271 (1983).

Habeeb et al, Prep. Biochem., 14(1), 1–17 (1984).

Pejaudier et al., Vox. Sang., 23, 165–175 (1972).

Steinbuch, M. et al., Prep. Biochem., 3(4), 363–373 (1973).

*Primary Examiner*—Morton Foelak
*Assistant Examiner*—Carlos Azpuru
*Attorney, Agent, or Firm*—James A. Giblin

[57] ABSTRACT

Lipid-enveloped viruses present in purified biologically active protein products obtained from blood or cell culture systems can be inactivated by contacting the products with caprylic acid at a non-ionized concentration, pH, temperature and ionic environment sufficient to inactivate the viruses without adversely precipitating or affecting the biological activity of the protein products.

18 Claims, 1 Drawing Sheet

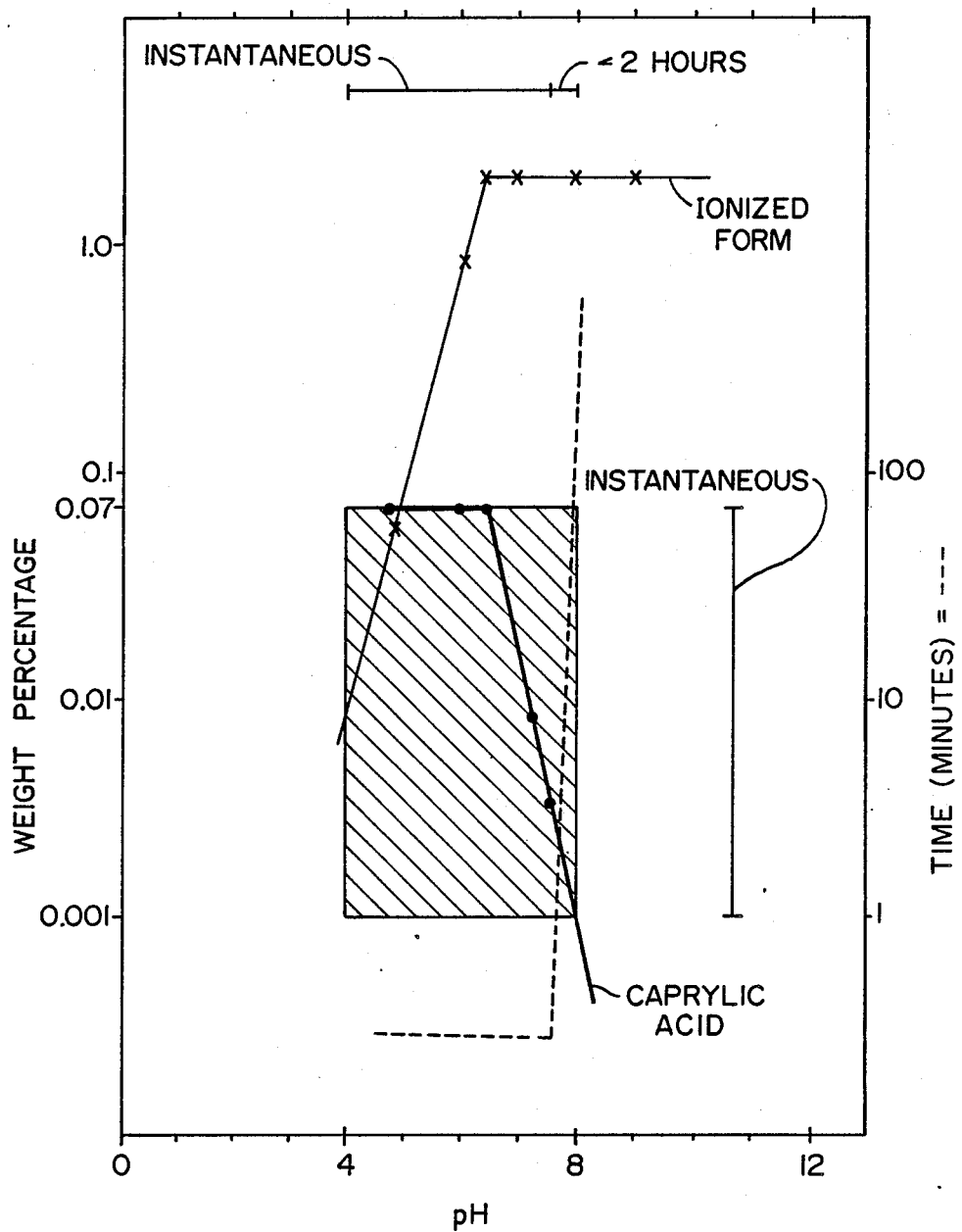

VIRAL INACTIVATION PROCESS

BACKGROUND OF THE INVENTION

1. Field:

This disclosure relates generally to viral inactivation processes and specifically to viral inactivation in biologically active, therapeutic proteinaceous products.

2. Prior Art:

The safety of pharmaceutical products is always a concern, especially in cases where viral contamination is possible (e.g. in products derived from blood, or cell culture systems designed to produce biologically active proteins). Unfortunately, the very products in which viruses are found are commonly labile and quite sensitive to many known and conventional viral inactivation techniques. Also, in some cases, efforts to protect the protein also protect the virus.

Various attempts have been made to overcome this situation. For example, it is well known that biologically active proteins can be rendered inactive by certain controlled heat treatments or specifically chosen chemical agents. Several heat treatment methods have been devised to inactivate viruses without adversely affecting the biological activity of the protein or significantly reducing its amount. See, for example, U.S. Pat. No. 4,440,679, to Fernandez and Lundblad (carbohydrate stabilizers for pasteurization of the very labile coagulation protein known as Factor VIII) and U.S. Pat. No. 4,762,714 to Mitra and Mozen (showing viral inactivation in an immune globulin product by controlled conditions of pH, temperature and time). See also, U.S. Pat. No. 4,456,590 to Reubenstein showing that Factor VIII can be subjected to pasteurization conditions (at least 60° C. for 10 hours) if first lyophilized, and U.S. Pat. No. 4,495,278 to Thomas (similar heat treatment of lyophilized Factor IX).

Various chemical methods have also been used to inactivate viruses. See, for example, U.S. Pat. No. 4,534,972, to Lembach (use of copper phenanthroline and related compounds) and U.S. Pat. No. 4,481,189 to Horowitz (use of tri-n-butyl phosphate and related compounds).

Carboxylic acids such as caprylic acid have been used in both the preparation of plasma products (precipitation of globulins) and even for the inactivation of lipid-coated virus, but not in the presence of therapeutic biologically active proteins (see J. A. Sands et al., Anti Microbial Agents and Chemotherapy, Jan. 1979, p. 134–136). Carboxylic acids (sodium caprylate) have also been used in combination with heat and amino acids for the viral inactivation of Factor VIII (see U.S. Pat. No. 4,446,134 to Naito et al.). See also, the sequential use of fatty acids for viral inactivation of plasma derivatives as disclosed by Horowitz et al., Vox. Sang. 54:14–20 (1988).

The precipitation of the bulk of the plasma proteins with caprylic acid without affecting IgG, ceruloplasmin and IgA has been described (Steinbuch, M. and Audran, R., Arch. Biochem. Biophys., 134, 279–294 [1969]). Human, equine, ovine and rabbit sera or plasma were diluted with 0.06 M acetate buffer to approximately 1.7% protein, adjusted to pH 4.8 at 20° C., and made 0.174 M (2.5 wt %) with respect to caprylic acid. Attention to buffer molarity (0.06M) and pH (pH 4.8±0.05) were critical to high purity IgG.

The precipitation method of Steinbuch, M., supra, has been applied to spent medium of hybridoma cultures and ascitic fluid from mice, using caprylic acid at a concentration of 0.066 M (0.86 wt %) for recovery of IgG (Russo, C., Callegaro, L., Lanza, E., Ferrone, S., J. Immunol. Methods, 65, 269–271 [1983]). The same method was applied to diluted human plasma adjusted to 0.15 M caprylic acid, or 2.16 wt %, (Habeeb, A.F.-S.A. and Francis, E.R., Prep. Biochem., 14(1), 1–17 [1984]).

IgA isolated from Cohn cold ethanol Fraction III by DEAE cellulose adsorption and elution was further purified for removal of alpha-2 macroglobulin by caprylic acid precipitation (Pejaudier, L., Audran, R. and Steinbuch, M., Vox Sang., 23, 165–175 [1972]). Parameters for precipitation consisted of 1.5 to 2.0% protein concentration adjusted to 0.9% sodium chloride, pH 5, and caprylic acid added at room temperature to 0.078 M or 1.12 wt %. The precipitated alpha-2 macroglobulin was removed by centrifugation.

Caprylic acid was used to precipitate most proteins and lipoproteins other than the immunoglobulins present in Cohn cold ethanol Fraction III (Steinbuch, M., Audran, R., Pejaudier, L., Blatrix, C., Prep. Biochem., 3(4), 363–373 [1973]). A suspension of Fraction III at approximately 2.5% protein was adjusted to 0.05 M acetate at pH 4.8 and brought to room temperature. Caprylic acid was added to 0.174 M or 2.5 wt % concentration. The resulting precipitate was discarded. The supernatant was enriched with IgG, IgM and IgA. It should be noted that in all cases where caprylic acid is used as a precipitating agent, it is present in an amount considerably above its maximum solubility in water under ideal conditions of pH, temperature and availability of caprylic acid (as discussed below). Such amounts, commonly about 0.86–2.5 wt %, are needed to assure sufficient quantity of the relatively insoluble caprylic acid in an insoluble form (an emulsion), thus useful as a precipitating agent.

Despite the above numerous publications, we are unaware of any method which uses caprylic acid in less than a precipitating concentration and alone to inactivate substantially all lipid-coated viruses without adversely affecting the biological activity or recoverable amount of therapeutic proteins. We have found that by carefully controlling the conditions of its use, we can use caprylic acid to inactivate lipid enveloped viruses in a biologically active therapeutic product without adversely affecting the activity of the product. Details of our findings are shown below.

SUMMARY OF THE INVENTION

The benefits of our method are based on the precise control of the amount of non-ionized caprylic acid generated according to the following dissociation reaction:

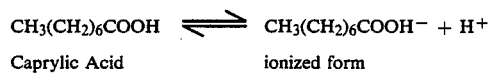

CH$_3$(CH$_2$)$_6$COOH ⇌ CH$_3$(CH$_2$)$_6$COO$^-$ + H$^+$
Caprylic Acid          ionized form Thus, our method of inactivating substantially all lipid-enveloped viruses in a labile, biologically active, proteinaceous, therapeutic product comprises the step of contacting the product with caprylic acid under conditions of concentration, pH and ionic environment sufficient to control the amount of non-ionized caprylic acid and still assure the inactivation of the viruses without adversely affecting the amount, biological activity and therapeutic efficacy of the product.

In a preferred embodiment, the inactivation procedure of the invention contemplates selective use of a caprylate salt concentration and pH to control the amount of caprylic acid generated without adversely affecting the stability or amount of the particular protein being inactivated. Undesirable loss of protein is avoided by assuring conditions which do not result in forming more than 0.068, or about 0.07% caprylic acid, its maximum solubility. Caprylic acid concentrations exceeding about 0.07% (wt % basis) can result in an emulsion of the caprylic acid and protein, thus resulting in undesirable protein loss. On the other hand, the amount of caprylic acid must be sufficient (at least 0.001 %) to assure inactivation of the lipid coated viruses within a reasonable time. Surprisingly, at lower pHs (6.5 or less) if caprylic acid is present at 0.07 to 0.001%, virus inactivation is achieved almost instantaneously. At higher pHs, where caprylate is clearly the dominant species, a higher concentration and a longer time is required to achieve the same log reduction of virus. Thus, in a preferred embodiment, the caprylic acid concentration useful for this invention ranges from about 0.07 to about 0.001% on a wt % basis.

The primary advantage of the invention is its versatility. At a low concentration the invention can be used at low pH to instantaneously inactivate certain viruses. The method also allows one to inactivate, if necessary, at higher pHs in higher concentrations and longer time. This allows one to select an inactivation at the most stable pH of the protein of interest so that the protein is not altered or destroyed during the virus inactivation. Thus, in preferred cases, caprylic acid concentration ranges from about 0.07 to 0.001% on a :;t/wt % basis in water, and this is controlled by controlling both the pH and amount of caprylate in ionized form (i.e. such as sodium caprylate) as discussed in more detail below.

Caprylic acid advantageously has a low, innocuous toxicity in humans, and it is presently being used as a stabilizer for albumin or plasma protein fraction (PPF) that is infused in large amounts into human patients Another advantage of the invention is that it assures the availability of virus-free therapeutically active proteins such as IgM/IgG which is purified from Cohn Fr. III paste, a notorious repository of plasma viruses A basic advantage is that it is a process that, when carefully controlled, is gentle to proteins and is applicable to any protein stable somewhere between about pH 4.0 and pH 8.0.

BRIEF DESCRIPTION OF THE FIGURE

The figure is a graph relating the concentration of caprylic acid to the pH and viral inactivation time of a given solution.

Detailed Description and Specific Embodiments

By standard biochemical convention and as used herein, the suffix '-ate' (i.e., caprylate) denotes any mixture of the acid and its ionized form, as in the dissociation reaction:

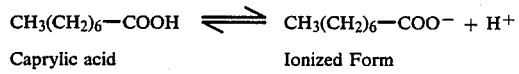

CH$_3$(CH$_2$)$_6$—COOH $\rightleftharpoons$ CH$_3$(CH$_2$)$_6$—COO$^-$ + H$^+$
Caprylic acid      Ionized Form The pKa of caprylic acid is 4.89 (CRC Handbook of Chemistry and Physics, 56th Edition). The Henderson-Hasselbalch equation:

$$pH = pKa + \log \frac{[\text{ionized form}]}{[\text{acid}]}$$

gives the concentration of acid and its ionized form at various pHs. Thus, one can easily provide a given concentration of caprylic acid by carefully controlling pH and caprylate concentration. For example, if the caprylic acid concentration is kept constant at 0.07% (0.0035 M) and the ionized form (e.g., sodium caprylate) is varied between 0.06% at pH 4.9 and 2.0% at pH=8, the amount of caprylic acid shown as FIG. 1 is produced. As used herein, caprylic acid refers to the non-ionized form of the acid (also known as octanoic acid).

We have found that it is relatively easy to achieve a practical and preferred concentration of caprylic acid. This can be done by varying the concentration of sodium caprylate between 0.1% at pH 4.8 and 20% at about pH=9.0 to give instantaneous inactivation of lipid-coated viruses. More preferably, the total concentration of caprylate is kept between 0.1% at pH 4.8 and linearly increasing to 2.0% at 6.5 to give instantaneous virus inactivation. Alternatively, the caprylate can be kept at 2% between pH 6.5 and 9.5 for a longer period of time (e.g., 2 to 4 hours) to give an appropriate caprylic acid concentration for virus inactivation. The premise here is that the non-ionized acid form (caprylic acid) is the active agent in virus kill by somehow affecting the lipid envelope or proteins embedded in it and that due to the dissociation reaction caprylic acid can be kept at a high enough concentration at higher pHs by increasing the concentration of the ionized form (sodium caprylate) to kill viruses.

The mixture of the protein composition and viral and bacterial inactivating agents is usually held at a temperature of about 2°-60° C. (preferably about 4°-20° C.) for a period of at least about 0.25 hours (preferably about 0.5-3 hours). As noted above, the treatment of the invention is carried out usually under pH conditions that are compatible with the protein material being treated. Thus, depending on the protein, the pH of the mixture should generally be within the range of about 4-10, preferably about 4.5 to 8.5, more preferably about 4.8 to 8.0 for most biologically active proteins. In general, pH and temperature ranges are chosen that ensure the least disturbance to the active protein in the composition are desirable. Those skilled in the art are familiar to the preferred pH ranges for a given protein.

Those experienced in the art would also add suitable stabilizers for the protein of interest during the treatment of the mixture as described above. The protein composition may be subsequently treated to remove the added caprylic acid/caprylate. Conventional techniques can be employed to achieve this end. For example, the mixture can be dialyzed or the protein of interest can be bound to anion exchange resin and washed to remove the added caprylic acid/caprylate with subsequent elution of the protein of interest. Other means of removing the agents will occur to those skilled in the art.

We have found that our viral inactivation treatment works on a wide variety of biologically active therapeutic proteins such as antibodies (plasma derived and monoclonal), human serum albumin, coagulation factors, fibronectin, and transferrin.

Definition of Terms

Caprylic acid means the non-ionized form as defined above. As used herein, the substantial reduction of infectivity means that the viral infectivity titer of a given preparation is reduced by at least about 4 logs or to a non-detectable (N.D.) level. Substantially instantaneous viral inactivation means that virus inactivation occurs before viral titer can be measured (e.g. it is N.D.) using prompt, conventional techniques. Without adversely affecting biological activity means that the contact with caprylic acid results in less than about 30% loss of original biological activity, as measured using conventional techniques for the biologically active protein of interest. Without adversely affecting the amount of the biologically active protein means that contact with the caprylic acid results in less than about 40% loss of the original protein amount (the pre-viral inactivation treatment amount). This is preferably less than about 10%. A lipid-enveloped virus, as used herein, means a virus the nucleic acid of which is encapsulated by a capsid which contains lipids. These are well known to those skilled in the art, as well as the expression lipid-enveloped (or coated) virus. Therapeutic means capable of providing a medically beneficial effect when administered to a mammal.

Examples of our disclosure are given below to show how variables such as concentrations of caprylic acid and caprylate, pH, temperature, time can affect reduction of viral infectivity, protein recovery, and biological activity retention of the protein.

EXAMPLE 1

Pseudomonas aeruginosa Monoclonal IgM antibody (Human) (Ps MAb-IgM) was produced by Epstein-Barr virus (EBV) transformed human B lymphocytes (A.T.C.C. CRL 8752). The pre-transformed cells were obtained from donors having naturally occurring antibody titers specific to one of the seven Fisher-Devlin serotypes, F-4. The antibody binds to a serotypic determinant on surface lipopolysaccharide molecules of that bacterium. Cell culture harvest for the F-4 antibody was clarified, partially purified and adjusted to pH 8 with 1 N NaOH At room temperature (R.T.) the IgM solution at 0.38 mg/ml (19 mg total) was initially contacted with Herpes Simplex Type I (HSV-1) virus and vesicular stomatitis virus (VSV). Thereafter 2.0 wt % sodium caprylate was added and the solution readjusted to pH 8 which by Henderson Hasselbalch calculation at pH 8 represents 0.0014 wt % caprylic acid and 1.9986 wt % caprylate in ionized form. After virus spiking the solution was held 60 minutes. Virus spiked pretreatment samples served as controls in this and subsequent examples.

Ps MAb-IgM F-4 protein yield values were based on radial immuno diffusion (RID) assays. Functional activity was established as specific lipo poly-saccharide (LPS) binding capacity. Studies in subsequent IgM F-4 Examples demonstrated substantially no loss of LPS binding capacity as well.

The results for Example 1 are shown in Table I:

TABLE I

| Temp. | Time (minutes) | IgM (F-4) mg | % Yield | LPS Binding Capacity % | Virus ($Log_{10}$ $TCID_{50}$/ml) HSV-1 | VSV |
|---|---|---|---|---|---|---|
| R.T. | 0 | 19 | 100 | 100 | 5.25 | 7.0 |
| | 60 | | | | N.D. | N.D. |
| | 120 | 19.2 | 101 | 98 | N.D. | N.D. |

N.D.: Not detectable (lower limit of detection ≠ ≦1.5)

EXAMPLE 2

Ps MAb IgM (F-4) was prepared and treated as in Example 1 with the exception that in addition to VSV, the study included Epstein Barr virus (EBV) and the inactivation step was carried out at a lower temperature (5° C.). After spiking with virus the solution was held 120 minutes.

The results for Example 2 are shown in Table II.

TABLE II

| Temperature | Time (Minutes) | IgM (F-4) mg | % Yield | Virus ($Log_{10}$ $TCID_{50}$/ml) VSV | EBV |
|---|---|---|---|---|---|
| 5° C. | 0 | 19 | 100 | 7.5 | 7.9 |
| | 60 | — | — | 5.75 | 3.7 |
| | 120 | 19.4 | 102 | 5.0 | N.T. |

N.T.: Not tested

EXAMPLE 3

Ps MAb IgM (F-4) was prepared as in Example 1 with the exception that the partially purified IgM solution for inactivation was at 5° C. and was adjusted to pH 4.8 with 1N HCl. The sample was initially contacted with virus and thereafter 0.1 wt % caprylic acid was added and re-adjusted to pH 4.8 with 1 N NaOH which by Henderson Hasselbalch calculation at pH 4.8 represents 0.055 wt % caprylic acid and 0.045 wt % caprylate in ionized form. After virus spiking the solution was held 60 minutes at 4° C.

The results for Example 3 are shown in Table III.

TABLE III

| Temperature | Time (Minutes) | IgM (F-4) mg | % Yield | Virus ($Log_{10}$ $TCID_{50}$/ml) HSV-1 | VSV |
|---|---|---|---|---|---|
| 5° C. | 0 | 9.5 | 100 | 6.75 | 7.5 |
| | 30 | | | 3.25 | 6.0 |
| | 60 | 10.3 | 108 | N.D. | 5.5 |

N.D.: Not detectable (lower limit of detection ≦1.5)

EXAMPLE 4

Pseudomonas exotoxin A antibody IgG (Human) (MAb Exo A IgG) was produced by EBV transformed human B lymphocytes (A.T.C.C. CRL 8833) obtained from donors having naturally occurring antibody titers to Pseudomonas aeruginosa exotoxin A. Cell culture harvest for MAb Exo A IgG was clarified and purified. At 5° C. the MAb Exo A IgG was adjusted to 0.5 mg/ml (25 mg total) at pH 6.5, was initially contacted with VSV and HSV-1 virus. Thereafter 2.0 wt % sodium caprylate was added and readjusted to pH 6.5 with 1N HCl which by Henderson Hasselbalch calculation at pH 6.5 represents 0.042 wt % caprylic acid and 1.958 wt % caprylate in ionized form. After spiking the solution was held 30 minutes.

The results for Example 4 are shown in Table IV.

TABLE IV

| Temperature | Treatment Time (minutes) | IgM (F-4) mg | % Yield | Virus (Log$_{10}$ TCID$_{50}$/ml) VSV | HSV-1 |
|---|---|---|---|---|---|
| 5° C. | 0 | 25 | 100 | 7.5 | 7.0 |
|  | 30 | 26 | 104 | N.D. | N.D. |

N.D.: Not Detectable (lower limit of detection ≦1.5)

EXAMPLE 5

MAb Exo A IgG was prepared as in Example 4 except that two concentrations of sodium caprylate were applied as indicated in Results. The samples for viral inactivation efficiency studies were at pH 6.3 and 5° C. for 60 minute contact. Virus species include VSV, HSV-1, vaccinia virus, and sindbis virus.

The results for the Example 5 are shown in Table V.

TABLE V

| Temperature | Treatment Time (minutes) | Virus (Log$_{10}$ TCID$_{50}$/ml) VSV A* | VSV B** | HSV-1 A | HSV-1 B | Vaccinia A | Vaccinia B | Sindbis A |
|---|---|---|---|---|---|---|---|---|
| 5° C. | 0 | 8.0 | 7.5 | 6.25 | 6.5 | 5.25 | 5.0 | 8.5 |
|  | 1 | — | 1.5 | — | ND | — | — | — |
|  | 10 | 2.75 | ND | ND | ND | 5.0 | — | — |
|  | 15 | — | — | — | — | — | ND | — |
|  | 20 | 2.5 | — | ND | — | 5.0 | — | — |
|  | 30 | 2.75 | — | — | — | 4.25 | — | ND |
|  | 60 | — | — | — | — | — | — | — |

ND Not Detectable (lower limit of detection ≦1.5)
A* Samples received 1.0 wt % sodium caprylate and were re-adjusted to pH 6.3 with 1N HCl which by Henderson Hasselbalch calculation at pH 6.3 represents 0.033 wt % caprylic acid and 0.967 wt % caprylate in ionized form.
B** Samples received 2.0 wt % sodium caprylate and were re-adjusted to pH 6.3 with 1N HCl which by Henderson Hasselbalch calculation at pH 6.3 represents 0.065 wt % caprylic acid and 1.935 wt % caprylate in ionized form.

EXAMPLE 6

Two Non-lipid coated viruses, Bovine Parvovirus (BPV) and Polio II, were reacted with caprylic acid to demonstrate lack of effectiveness in contrast to inactivation of lipid coated viruses. Ps MoAb IgM (F-4) was prepared and chemically treated as in Example 1 with the exception that the inactivation temperature was 5° C. and the virus was BPV. MoAb Exo A IgG was prepared and chemically treated as in Example 5 with the exception that the IgG solution was adjusted to pH 6.3. The IgG samples were initially contacted with BPV and Polio II viruses and thereafter sodium caprylate was added to 2.0 wt % and readjusted to pH 6.3 with 1N HCl which by Henderson Hasselbalch calculation at pH 6.3 consists of 0.065 wt % caprylic acid and 1.935 wt % caprylate in ionized form. After virus spiking the solutions were held 120 minutes.

The results for Example 6 are shown in Table VI.

TABLE VI

| Temperature | Treatment Time (minutes) | Virus (Log$_{10}$ TCID$_{50}$/ml) Ps MoAb IgM BPV | MAb Exo A IgG BPV | MAb Exo A IgG Polio II |
|---|---|---|---|---|
| 5° C. | 0 | 2.75 | 3.5 | 6.0 |
|  | 30 | 3.75 | 3.25 | — |
|  | 60 | 3.0 | 3.25 | 6.25 |
|  | 120 | 3.25 | 3.5 | 6.5 |

EXAMPLE 7

Human serum albumin was isolated from Supernatant IV-4 of the cold ethanol purification method of E. J. Cohn. The albumin was adjusted to a concentration of 0.5 mg/ml (25 mg total) at pH 6.0. At 4° C. the albumin solution was contacted by Vesicular Stomatitis virus (VSV) and thereafter sodium caprylate was added to 1.0 wt % and re-adjusted to pH 6.0 with 1N HCl which by Henderson Hasselbalch calculation at pH 6 represents 0.062 wt % caprylic acid and 0.938 wt % caprylate in ionized form. After virus spiking the solution was held 60 minutes.

The results for Example 7 are show in Table VII.

TABLE VII

| Temperature | Time (minutes) | Albumin mg | % Yield | VSV (Log$_{10}$ TCID$_{50}$/ml) |
|---|---|---|---|---|
| 4° C. | 0 | 25 | 100 | 6.75 |
|  | 60 | 24.75 | 99 | N.D. |

N.D.: Not detectable (lower limit of detection ≦1.5)

EXAMPLE 8

Human serum protein enriched with labile coagulation factors II, VII, IX and X was separated by anion exchange adsorption from Effluent I of the cold ethanol purification method of E. J. Cohn. The eluted coagulation factors were further purified and adjusted to a protein concentration of 1.73 mg/ml at pH 6.8. Sodium caprylate was added to a concentration of 2.0 wt % and readjusted to pH 6.8 with 1N HCl which by Henderson Hasselbalch calculation at pH 6.8 represents 0.022 wt % caprylic acid and 1.978 wt % caprylate in ionized form. After incubation at 4° C. for 2 hours the coagulation proteins were separated from chemical reactants by size exclusion chromatography using Sephadex G-50. The yield results based on functional coagulation activity are shown in Table VIII.

TABLE VIII

| Temperature | Time (minutes) | Sample Description | Coagulation Factors (units/ml) II | VII | IX | X |
|---|---|---|---|---|---|---|
| 5° C. | 0 | Untreated | 1.82 | 0.17 | 1.59 | 2.09 |
|  | 120 | Treated | 1.89 | 0.19 | 1.60 | 2.12 |
|  |  | Percent Functional Yield | 104 | 112 | 101 | 101 |

EXAMPLE 9

Protein enriched in fibronectin is isolated from a discard protein fraction during the purification of human Factor VIII from cryoprecipitate. The fibronectin was adjusted to a protein concentration of 1.34 mg/ml at pH 6.9 (33.5 mg total). Sodium caprylate was added to a concentration of 2.0 wt % and readjusted to pH 6.9 with 1N HCl which by Henderson Hasselbalch equation at pH 6.9 represents 0.014 wt % caprylic acid and 1.986 wt % caprylate in ionized form. After incubation at 5° C. for one hour the fibronectin was separated from chemical reactants by size exclusion chromatography using Sephadex G-50. Samples before and after caprylic acid treatment were assayed by Enzyme-linked immunosorbent assay to establish yield and were analyzed for structural changes by fast protein liquid chromatography (FPLC). Results for example 9 are shown below in Table IX.

TABLE IX

| Temperature | Time (minutes) | Fibronectin mg | % Yield |
|---|---|---|---|
| 5° C. | 0 | 33.5 | 100 |

TABLE IX-continued

| Temperature | Time (minutes) | Fibronectin mg | % Yield |
|---|---|---|---|
| | 60 | 32.7 | 97.8 |

EXAMPLE 10

Transferrin, also known as alpha$_1$ metal-combining globulin, was isolated from Fraction IV-1 from the cold ethanol purification method of E.J. Cohn. The Transferrin was adjusted to 3.35 mg/ml (105 mg total) at pH 6.8. Sodium caprylate was added to a concentration of 2.0 wt % and readjusted pH to 6.8 with 1N HCl which by Henderson Hasselbalch calculation at pH 6.8 represents 0.022 wt % caprylic acid and 1.978 wt % caprylate in ionized form. After incubation at 5° C. for 60 minutes, the fibronectin was separated from chemical reactants by size exclusion chromatography using Sephadex G-50. Samples before and after caprylic acid treatment were assayed by RID to establish yield and were analyzed for structural changes by FPLC. Results for experiment 10 are shown in Table X.

TABLE X

| Temperature | Time (minutes) | Transferrin mg | % Yield | Structural Changes Aggregates | Fragments |
|---|---|---|---|---|---|
| 5° C. | 0 | 105 | 100 | N.D. | N.D. |
| | 60 | 108 | 103 | N.D. | N.D. |

N.D.: Not Detectable

EXAMPLE 11

Cryoprecipitate was recovered by centrifugation from thawed pools of fresh frozen human plasma. Coagulation Factor VIII, also known as Antihemophilic Factor (AHF), was recovered from the cryoprecipitate and purified. The purified AHF solution was adjusted to an AHF concentration of 1.7 units/ml (46.2 AHF units total) at pH 7.2. At 5° C. sodium caprylate was added to a concentration of 2.0 wt % and readjusted to pH 7.2 with 1N HCl which by Henderson Hasselbalch calculation at pH 7.2 represents 0.0087 wt % caprylic acid and 1.9913 wt % caprylate in ionized form. After incubation at 5° C. for 2 hours the AHF enriched protein was separated from chemical reactants by size exclusion chromatography using Sephadex G-50. The yield results based on functional Factor VIII coagulation activity are shown in Table XI.

TABLE XI

| Temperature | Time (minutes) | Factor VIII Total Units | % Yield |
|---|---|---|---|
| 5° C. | 0 | 46.2 | 100 |
| | 120 | 27.2 | 59 |

EXAMPLE 12

Human plasma derived Immune Globulin M (IgM-pd) purified from Fraction III was studied to resolve the role of low pH (pH 4.8) in virus destruction. Fraction III paste was processed from normal human plasma by the Cohn-Oncley cold ethanol fractionation method. Fraction III paste was suspended by mixing at 20° C. in 0.05 M sodium acetate at pH 4.0. Insoluble proteins were removed by centrifugation and filtration. The clarified filtrate, enriched in IgM-pd was adjusted to pH 4.8. At 5° C. the IgM-pd solution was contacted by VSV. A tissue culture (T.C.) media sample was contacted by VSV as a control. Caprylic acid was not added to either sample. After virus spiking the samples were tested for infectivity at intervals up to 8 hours. Results for Example 12 are presented in Table XII.

TABLE XII

| Temp. | Time (hours) | Infectivity ($Log_{10}TCID_{50}$/ml) IgM-pd | T.C. Control |
|---|---|---|---|
| 5° C. | 0 | 6.75 | 8.0 |
| | 2 | 6.75 | N.T. |
| | 6 | 7.25 | N.T. |
| | 8 | $\geq 6.5$ | 7.5 |

N.T.: Not tested

Given the above disclosure and examples, variations will occur to those skilled in the art. Accordingly, it is intended that the invention disclosed here in should be limited only by the following claims.

We claim:

1. A method of inactivating a lipid-enveloped virus in a solution of biologically active therapeutic proteins, the method comprising the step of contacting the solution with caprylic acid under conditions sufficient to substantially reduce the infectivity of the virus without adversely affecting the amount and biological activity of the proteins.

2. The method of claim 1 wherein the caprylic acid is in the non-ionized form in an amount ranging from about 0.07 to about 0.001%, on a wt % basis in water.

3. The method of claim 1 wherein the infectivity is reduced to a non-detectable level.

4. The method of claim 1 wherein loss, if any, of the biological activity of the treated protein is less than about 30% of the original activity.

5. The method of claim 1 wherein the caprylic acid concentration ranges from about 0.07% to about 0.001% on a wt % basis, in water and the pH ranges from about 4 to about 8 .

6. The method of claim 1 wherein the solution includes caprylate ions and conditions of the caprylate ion concentration and solution pH are such that the concentration of caprylic acid is maintained between about 0.07% and 0.001% on a wt % basis, in water.

7. The method of claim i wherein the concentration of caprylic acid ranges from 0.07% to 0.01%, on a wt % basis, in water.

8. The method of claim 1 wherein the micro organism is a lipid coated virus selected from HSV-1, VSV, vaccinia, Sindbis, and EBV.

9. The method of claim 1 wherein the biologically active protein is one or more of the antibodies, human serum albumin, coagulation factors, fibronectin, and transferrin.

10. The method of claim 9 where the coagulation factor is selected from factors II, VII, VIII, IX and X.

11. A method of inactivating lipid-enveloped viruses in an aqueous solution of antibodies, the method comprising the step of contacting the solution with caprylic acid at a concentration ranging from about 0.07 to about 0.001% on a wt % basis for a time and at a pH sufficient to substantially reduce infectivity of the virus.

12. The method of claim 11 wherein the antibody is an IgM antibody and the pH of the solution is about 8.0.

13. The method of claim 11 wherein the antibody is an IgG antibody and the pH is about 6.3.

14. A method of inactivating a lipid-enveloped viruses in an aqueous solution of biologically active, human monoclonal antibodies, the method comprising the step of contacting the viruses with caprylic acid at a concentration ranging from about 0.07% to about 0.001% on at wt % basis for a time sufficient to reduce to virus titer to a non-detectable level.

15. The method of claim 14 wherein the antibodies are antibodies which bind to a serotype determinant on the lipopolysaccharide molecules of a *Pseudomonas aeruoinosa* bacterium.

16. The method of claim 15 the bacterium is one of the Fisher-Devlin immunotypes 1 to 7.

17. The method of claim 16 wherein the bacterium is Fisher immunotype 4.

18. The method of claim 14 wherein the antibodies are antibodies which bind to exotoxin A of *Pseudomonas aeruoinosa*.

* * * * *

UNITED STATES PATENT AND TRADEMARK OFFICE
CERTIFICATE OF CORRECTION

PATENT NO. : 4,939,176

DATED : July 3, 1990

INVENTOR(S) : Richard L. Seng and John L. Lundblad

It is certified that error appears in the above-identified patent and that said Letters Patent is hereby corrected as shown below:

Column 3, line 36 should read

--ranges from about 0.07 to 0.001% on a wt/wt% basis in--

Signed and Sealed this

Twenty-fifth Day of February, 1992

Attest:

HARRY F. MANBECK, JR.

Attesting Officer  Commissioner of Patents and Trademarks